US008597915B2

(12) United States Patent
Hauer et al.

(10) Patent No.: US 8,597,915 B2
(45) Date of Patent: Dec. 3, 2013

(54) PROCESS FOR THE REDUCTION OF CINNAMALDEHYDE DERIVATIVE EMPLOYING ENOATE REDUCTASES

(75) Inventors: Bernhard Hauer, Fussgönheim (DE); Rainer Stürmer, Rödersheim-Gronau (DE); Clemens Stückler, Graz (AT); Kurt Faber, Graz (AT)

(73) Assignee: BASF SE (DE)

( * ) Notice: Subject to any disclaimer, the term of this patent is extended or adjusted under 35 U.S.C. 154(b) by 0 days.

(21) Appl. No.: 13/576,280

(22) PCT Filed: Feb. 1, 2011

(86) PCT No.: PCT/EP2011/051406
§ 371 (c)(1),
(2), (4) Date: Jul. 31, 2012

(87) PCT Pub. No.: WO2011/092345
PCT Pub. Date: Aug. 4, 2011

(65) Prior Publication Data
US 2012/0301931 A1 Nov. 29, 2012

(30) Foreign Application Priority Data
Feb. 1, 2010 (EP) .................................... 10152321

(51) Int. Cl.
*C12P 7/24* (2006.01)
*C12P 17/06* (2006.01)

(52) U.S. Cl.
USPC .......................................... 435/125; 435/147

(58) Field of Classification Search
None
See application file for complete search history.

(56) References Cited

U.S. PATENT DOCUMENTS

| | | | |
|---|---|---|---|
| 6,596,520 B1 | 7/2003 | Friedrich et al. | |
| 8,329,438 B2 * | 12/2012 | Savile et al. | 435/189 |
| 2010/0190218 A1 * | 7/2010 | Savile et al. | 435/128 |
| 2010/0291640 A1 | 11/2010 | Stuermer et al. | |
| 2010/0291641 A1 | 11/2010 | Dauwel et al. | |
| 2011/0137002 A1 | 6/2011 | Hauer et al. | |
| 2011/0171700 A1 | 7/2011 | Breuer et al. | |
| 2012/0070867 A1 | 3/2012 | Maurer et al. | |
| 2012/0123155 A1 | 5/2012 | Hauer et al. | |
| 2012/0135477 A1 | 5/2012 | Breuer et al. | |
| 2012/0171738 A1 | 7/2012 | Hauer et al. | |

FOREIGN PATENT DOCUMENTS

| | | |
|---|---|---|
| DE | 100193773 | 4/2001 |
| EP | 1069183 A2 | 1/2001 |
| EP | 1149849 A1 | 10/2001 |
| WO | WO-2009007460 A2 | 1/2009 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
U.S. Appl. No. 13/496,086, filed Mar. 14, 2012.
U.S. Appl. No. 13/497,985, filed Mar. 23, 2012.
Chapuis, et al., Appl. Catal. A. Gen., 2001, 221, pp. 93-117.
Abate, et al., Chem. Biodivers., 2004, 1, pp. 1888-1898.
Doszczak, et al., Angew. Chem. Int. Ed., 2007, 46, pp. 3367-3371.
Brenna et al., Tetrahedron: Asymmetry, 2003, 14, pp. 1-42.
Akutagawa, Appl. Catal. A: Gen. 1995, 128, pp. 171-207.
Bovo, et al., Synthesis 2008, pp. 2547-2550.
Knowles, et al., Acc. Chem. Res. 2007, 40, pp. 1238-1239.
Adolfsson, Angew. Chem. Int. Ed. 2005, 44, pp. 3340-3342.
Akagawa, et al., Tetrahedron: Asymmetry 2009, 20, pp. 461-466.
Majeric, et al., Biotechnol. Lett. 1995, 17, pp. 1189-1194.
Fuganti, et al., J. Chem. Soc. Perkin Trans. 1, 2000, pp. 3758-3764.
D'Arrigo, et al., Tetrahedron 1998, 54, pp. 15017-15026.
Fronza, et al., J. Org. Chem. 1982, 47, pp. 3289-3296.
Fronza, et al., Tetrahedron: Asymmetry 2004, 15, pp. 3073-3077.
Chaparro-Riggers, et al., Adv. Synlh. Calal. 2007, 349, pp. 1521-1531.
Kataoka, et al., J. Biolechnol. 2004, 114, pp. 1-9.
Hall, et al., Angew. Chern. Int. Ed. 2007, 46, pp. 3934-3937.
Hall, et al., Adv. Synlh. Calal. 2008, 350, pp. 411-418.
Hall, et al., Eur. J. Org. Chern. 2008, pp. 1511-1516.
Saudan, Acc. Chem. Res. 2007, 40, pp. 1309-1319.
Minnaard, et al., Acc. Chem. Res. 2007, 40, pp. 1267-1277.
Yang, et al., Angew. Chem. Int. Ed. 2005, 44, pp. 108-110.
Ouellet, et al., Acc. Chem. Res. 2007, 40, pp. 1327-1339.
Watson, et al., J. Am. Chem. Soc. 2009, 131, pp. 14584-14589.
Tungler, et al., Curro Org. Chem. 2006, 10, pp. 1569-1583.
Serra, et al., Trends Biotechnol. 2005, 23, pp. 193-198.
Sunjic, et al., Croat. Chem. Acta 1996, 69, pp. 643-660.
Stuermer, et al., Curro Opin. Chern. Bioi. 2007, 11, pp. 203-213.
Padhi, et al., J. Arn. Chern. Soc. 2009, 131, pp. 3271-3280.
Müller, et al., Biolechnol. Bioeng. 2007, 98, pp. 22-29.
International Search Report for PCT/EP2011/051406 mailed Jun. 10, 2011.
International Preliminary Report on Patentability for PCT/EP2011/051406 mailed Apr. 17, 2012.

* cited by examiner

*Primary Examiner* — Tekchand Saidha
*Assistant Examiner* — Md. Younus Meah
(74) *Attorney, Agent, or Firm* — Novak Druce Connolly Bove + Quigg LLP

(57) ABSTRACT

The present invention relates to a novel enzymatically catalyzed method for the production of asymmetric aromatic aldehydes in an aqueous reaction medium containing certain organic co-solvents.

10 Claims, 1 Drawing Sheet

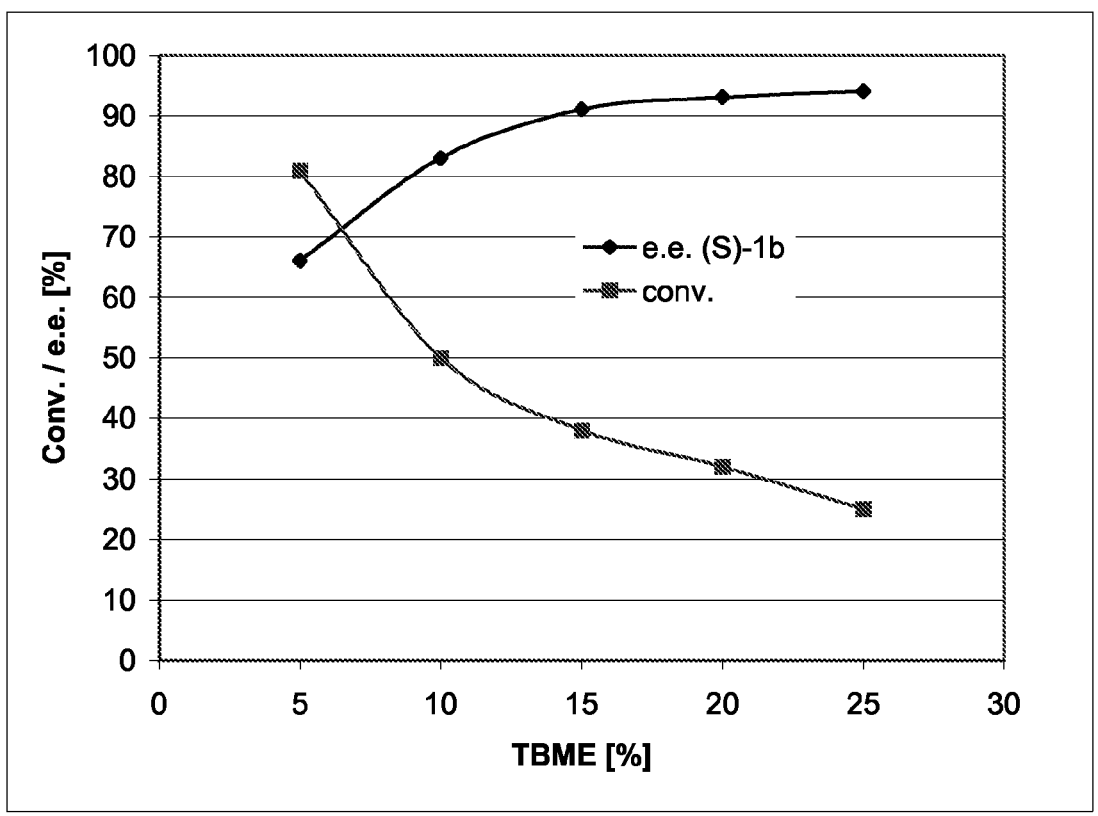

SEQUENCE LISTING

<160> NUMBER OF SEQ ID NOS: 7

<210> SEQ ID NO 1
<211> LENGTH: 400
<212> TYPE: PRT
<213> ORGANISM: Saccharomyces carlsbergensis

<400> SEQUENCE: 1

```
Met Ser Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
    50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Val Trp Ser Glu Glu Gln Met Val
                85                  90                  95

Glu Trp Thr Lys Ile Phe Asn Ala Ile His Glu Lys Lys Ser Phe Val
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Phe Met
    130                 135                 140

Asp Ala Glu Gln Glu Ala Lys Ala Lys Lys Ala Asn Asn Pro Gln His
145                 150                 155                 160

Ser Leu Thr Lys Asp Glu Ile Lys Gln Tyr Ile Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Thr Arg Thr Asp Glu Tyr Gly Gly Ser Ile Glu Asn Arg Ala Arg Phe
    210                 215                 220

Thr Leu Glu Val Val Asp Ala Leu Val Glu Ala Ile Gly His Glu Lys
225                 230                 235                 240
```

```
Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Ala Gly Glu
            260                 265                 270

Leu Glu Lys Arg Ala Lys Ala Gly Lys Arg Leu Ala Phe Val His Leu
            275                 280                 285

Val Glu Pro Arg Val Thr Asn Pro Phe Leu Thr Glu Gly Glu Gly Glu
            290                 295                 300

Tyr Glu Gly Gly Ser Asn Asp Phe Val Tyr Ser Ile Trp Lys Gly Pro
305                 310                 315                 320

Val Ile Arg Ala Gly Asn Phe Ala Leu His Pro Glu Val Val Arg Glu
            325                 330                 335

Glu Val Lys Asp Lys Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
            355                 360                 365

Lys Tyr Asp Arg Asp Thr Phe Tyr Gln Met Ser Ala His Gly Tyr Ile
            370                 375                 380

Asp Tyr Pro Thr Tyr Glu Ala Leu Lys Leu Gly Trp Asp Lys Lys
385                 390                 395                 400

<210> SEQ ID NO 2
<211> LENGTH: 400
<212> TYPE: PRT
<213> ORGANISM: Saccharomyces cerevisiae

<400> SEQUENCE: 2

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
            35                  40                  45

Pro Asn Arg Asp Trp Ala Val Glu Tyr Tyr Ala Gln Arg Ala Gln Arg
        50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
210                 215                 220
```

```
Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
            275                 280                 285

Val Glu Pro Arg Val Thr Asn Pro Phe Leu Thr Glu Gly Glu Gly Glu
        290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Asn
385                 390                 395                 400

<210> SEQ ID NO 3
<211> LENGTH: 400
<212> TYPE: PRT
<213> ORGANISM: Saccharomyces cerevisiae

<400> SEQUENCE: 3

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Trp Ser Leu Gly Trp Ala Ser Phe Pro Asp Val Leu
    115                 120                 125

Ala Arg Asp Gly Leu Arg Tyr Asp Cys Ala Ser Asp Arg Val Tyr Met
130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
            165                 170                 175

Ala Ala Lys Asn Ser Ile Ala Ala Gly Ala Asp Gly Val Glu Ile His
        180                 185                 190

Ser Ala Asn Gly Tyr Leu Leu Asn Gln Phe Leu Asp Pro His Ser Asn
    195                 200                 205
```

```
Lys Arg Thr Asp Glu Tyr Gly Gly Thr Ile Glu Asn Arg Ala Arg Phe
    210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
                260                 265                 270

Leu Glu Lys Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Gly Leu Pro Leu Asn
            355                 360                 365

Lys Tyr Asp Arg Ser Thr Phe Tyr Thr Met Ser Ala Glu Gly Tyr Thr
    370                 375                 380

Asp Tyr Pro Thr Tyr Glu Ala Val Asp Leu Gly Trp Asn Lys Asn
385                 390                 395                 400

<210> SEQ ID NO 4
<211> LENGTH: 376
<212> TYPE: PRT
<213> ORGANISM: Solanum lycopersicon

<400> SEQUENCE: 4

Met Glu Asn Lys Val Val Glu Lys Gln Val Asp Lys Ile Pro Leu
1               5                   10                  15

Met Ser Pro Cys Lys Met Gly Lys Phe Glu Leu Cys His Arg Val Val
            20                  25                  30

Leu Ala Pro Leu Thr Arg Gln Arg Ser Tyr Gly Tyr Ile Pro Gln Pro
        35                  40                  45

His Ala Ile Leu His Tyr Ser Gln Arg Ser Thr Asn Gly Gly Leu Leu
    50                  55                  60

Ile Gly Glu Ala Thr Val Ile Ser Glu Thr Gly Ile Gly Tyr Lys Asp
65                  70                  75                  80

Val Pro Gly Ile Trp Thr Lys Glu Gln Val Glu Ala Trp Lys Pro Ile
                85                  90                  95

Val Asp Ala Val His Ala Lys Gly Gly Ile Phe Phe Cys Gln Ile Trp
            100                 105                 110

His Val Gly Arg Val Ser Asn Lys Asp Phe Gln Pro Asn Gly Glu Asp
        115                 120                 125

Pro Ile Ser Cys Thr Asp Arg Gly Leu Thr Pro Gln Ile Arg Ser Asn
    130                 135                 140

Gly Ile Asp Ile Ala His Phe Thr Arg Pro Arg Arg Leu Thr Thr Asp
145                 150                 155                 160

Glu Ile Pro Gln Ile Val Asn Glu Phe Arg Val Ala Ala Arg Asn Ala
                165                 170                 175

Ile Glu Ala Gly Phe Asp Gly Val Glu Ile His Gly Ala His Gly Tyr
            180                 185                 190
```

```
Leu Ile Asp Gln Phe Met Lys Asp Gln Val Asn Asp Arg Ser Asp Lys
            195                 200                 205

Tyr Gly Gly Ser Leu Glu Asn Arg Cys Arg Phe Ala Leu Glu Ile Val
    210                 215                 220

Glu Ala Val Ala Asn Glu Ile Gly Ser Asp Arg Val Gly Ile Arg Ile
225                 230                 235                 240

Ser Pro Phe Ala His Tyr Asn Glu Ala Gly Asp Thr Asn Pro Thr Ala
                245                 250                 255

Leu Gly Leu Tyr Met Val Glu Ser Leu Asn Lys Tyr Asp Leu Ala Tyr
            260                 265                 270

Cys His Val Val Glu Pro Arg Met Lys Thr Ala Trp Glu Lys Ile Glu
        275                 280                 285

Cys Thr Glu Ser Leu Val Pro Met Arg Lys Ala Tyr Lys Gly Thr Phe
    290                 295                 300

Ile Val Ala Gly Gly Tyr Asp Arg Glu Asp Gly Asn Arg Ala Leu Ile
305                 310                 315                 320

Glu Asp Arg Ala Asp Leu Val Ala Tyr Gly Arg Leu Phe Ile Ser Asn
                325                 330                 335

Pro Asp Leu Pro Lys Arg Phe Glu Leu Asn Ala Pro Leu Asn Lys Tyr
            340                 345                 350

Asn Arg Asp Thr Phe Tyr Thr Ser Asp Pro Ile Val Gly Tyr Thr Asp
        355                 360                 365

Tyr Pro Phe Leu Glu Thr Met Thr
    370                 375

<210> SEQ ID NO 5
<211> LENGTH: 396
<212> TYPE: PRT
<213> ORGANISM: Solanum lycopersicon

<400> SEQUENCE: 5

Met Ala Ser Ser Ala Gln Asp Gly Asn Asn Pro Leu Phe Ser Pro Tyr
1               5                   10                  15

Lys Met Gly Lys Phe Asn Leu Ser His Arg Val Val Leu Ala Pro Met
            20                  25                  30

Thr Arg Cys Arg Ala Leu Asn Asn Ile Pro Gln Ala Ala Leu Gly Glu
        35                  40                  45

Tyr Tyr Glu Gln Arg Ala Thr Ala Gly Gly Phe Leu Ile Thr Glu Gly
    50                  55                  60

Thr Met Ile Ser Pro Thr Ser Ala Gly Phe Pro His Val Pro Gly Ile
65                  70                  75                  80

Phe Thr Lys Glu Gln Val Arg Glu Trp Lys Lys Ile Val Asp Val Val
                85                  90                  95

His Ala Lys Gly Ala Val Ile Phe Cys Gln Leu Trp His Val Gly Arg
            100                 105                 110

Ala Ser His Glu Val Tyr Gln Pro Ala Gly Ala Ala Pro Ile Ser Ser
        115                 120                 125

Thr Glu Lys Pro Ile Ser Asn Arg Trp Arg Ile Leu Met Pro Asp Gly
    130                 135                 140

Thr His Gly Ile Tyr Pro Lys Pro Arg Ala Ile Gly Thr Tyr Glu Ile
145                 150                 155                 160

Ser Gln Val Val Glu Asp Tyr Arg Arg Ser Ala Leu Asn Ala Ile Glu
                165                 170                 175

Ala Gly Phe Asp Gly Ile Glu Ile His Gly Ala His Gly Tyr Leu Ile
            180                 185                 190
```

```
Asp Gln Phe Leu Lys Asp Gly Ile Asn Asp Arg Thr Asp Glu Tyr Gly
            195                 200                 205

Gly Ser Leu Ala Asn Arg Cys Lys Phe Ile Thr Gln Val Val Gln Ala
            210                 215                 220

Val Val Ser Ala Ile Gly Ala Asp Arg Val Gly Val Arg Val Ser Pro
225                 230                 235                 240

Ala Ile Asp His Leu Asp Ala Met Asp Ser Asn Pro Leu Ser Leu Gly
                245                 250                 255

Leu Ala Val Val Glu Arg Leu Asn Lys Ile Gln Leu His Ser Gly Ser
            260                 265                 270

Lys Leu Ala Tyr Leu His Val Thr Gln Pro Arg Tyr Val Ala Tyr Gly
            275                 280                 285

Gln Thr Glu Ala Gly Arg Leu Gly Ser Glu Glu Glu Ala Arg Leu
            290                 295                 300

Met Arg Thr Leu Arg Asn Ala Tyr Gln Gly Thr Phe Ile Cys Ser Gly
305                 310                 315                 320

Gly Tyr Thr Arg Glu Leu Gly Ile Glu Ala Val Ala Gln Gly Asp Ala
                325                 330                 335

Asp Leu Val Ser Tyr Gly Arg Leu Phe Ile Ser Asn Pro Asp Leu Val
                340                 345                 350

Met Arg Ile Lys Leu Asn Ala Pro Leu Asn Lys Tyr Asn Arg Lys Thr
            355                 360                 365

Phe Tyr Thr Gln Asp Pro Val Val Gly Tyr Thr Asp Tyr Pro Phe Leu
            370                 375                 380

Gln Gly Asn Gly Ser Asn Gly Pro Leu Ser Arg Leu
385                 390                 395

<210> SEQ ID NO 6
<211> LENGTH: 338
<212> TYPE: PRT
<213> ORGANISM: Bacillus subtilis NamA

<400> SEQUENCE: 6

Met Ala Arg Lys Leu Phe Thr Pro Ile Thr Ile Lys Asp Met Thr Leu
1               5                   10                  15

Lys Asn Arg Ile Val Met Ser Pro Met Cys Met Tyr Ser Ser His Glu
            20                  25                  30

Lys Asp Gly Lys Leu Thr Pro Phe His Met Ala His Tyr Ile Ser Arg
        35                  40                  45

Ala Ile Gly Gln Val Gly Leu Ile Ile Val Glu Ala Ser Ala Val Asn
    50                  55                  60

Pro Gln Gly Arg Ile Thr Asp Gln Asp Leu Gly Ile Trp Ser Asp Glu
65                  70                  75                  80

His Ile Glu Gly Phe Ala Lys Leu Thr Glu Gln Val Lys Glu Gln Gly
                85                  90                  95

Ser Lys Ile Gly Ile Gln Leu Ala His Ala Gly Arg Lys Ala Glu Leu
            100                 105                 110

Glu Gly Asp Ile Phe Ala Pro Ser Ala Ile Ala Phe Asp Glu Gln Ser
        115                 120                 125

Ala Thr Pro Val Glu Met Ser Ala Glu Lys Val Lys Glu Thr Val Gln
    130                 135                 140

Glu Phe Lys Gln Ala Ala Ala Arg Ala Lys Glu Ala Gly Phe Asp Val
145                 150                 155                 160

Ile Glu Ile His Ala Ala His Gly Tyr Leu Ile His Glu Phe Leu Ser
                165                 170                 175
```

```
Pro Leu Ser Asn His Arg Thr Asp Glu Tyr Gly Gly Ser Pro Glu Asn
            180                 185                 190

Arg Tyr Arg Phe Leu Arg Glu Ile Ile Asp Glu Val Lys Gln Val Trp
        195                 200                 205

Asp Gly Pro Leu Phe Val Arg Val Ser Ala Ser Asp Tyr Thr Asp Lys
    210                 215                 220

Gly Leu Asp Ile Ala Asp His Ile Gly Phe Ala Lys Trp Met Lys Glu
225                 230                 235                 240

Gln Gly Val Asp Leu Ile Asp Cys Ser Ser Gly Ala Leu Val His Ala
                245                 250                 255

Asp Ile Asn Val Phe Pro Gly Tyr Gln Val Ser Phe Ala Glu Lys Ile
            260                 265                 270

Arg Glu Gln Ala Asp Met Ala Thr Gly Ala Val Gly Met Ile Thr Asp
        275                 280                 285

Gly Ser Met Ala Glu Glu Ile Leu Gln Asn Gly Arg Ala Asp Leu Ile
    290                 295                 300

Phe Ile Gly Arg Glu Leu Leu Arg Asp Pro Phe Phe Ala Arg Thr Ala
305                 310                 315                 320

Ala Lys Gln Leu Asn Thr Glu Ile Pro Ala Pro Val Gln Tyr Glu Arg
                325                 330                 335

Gly Trp

<210> SEQ ID NO 7
<211> LENGTH: 358
<212> TYPE: PRT
<213> ORGANISM: Zymomonas mobilis

<400> SEQUENCE: 7

Met Pro Ser Leu Phe Asp Pro Ile Arg Phe Gly Ala Phe Thr Ala Lys
1               5                   10                  15

Asn Arg Ile Trp Met Ala Pro Leu Thr Arg Gly Arg Ala Thr Arg Asp
            20                  25                  30

His Val Pro Thr Glu Ile Met Ala Glu Tyr Tyr Ala Gln Arg Ala Ser
        35                  40                  45

Ala Gly Leu Ile Ile Ser Glu Ala Thr Gly Ile Ser Gln Glu Gly Leu
    50                  55                  60

Gly Trp Pro Tyr Ala Pro Gly Ile Trp Ser Asp Ala Gln Val Glu Ala
65                  70                  75                  80

Trp Leu Pro Ile Thr Gln Ala Val His Asp Ala Gly Gly Leu Ile Phe
                85                  90                  95

Ala Gln Leu Trp His Met Gly Arg Met Val Pro Ser Asn Val Ser Gly
            100                 105                 110

Met Gln Pro Val Ala Pro Ser Ala Ser Gln Ala Pro Gly Leu Gly His
        115                 120                 125

Thr Tyr Asp Gly Lys Lys Pro Tyr Val Ala Arg Ala Leu Arg Leu
    130                 135                 140

Asp Glu Ile Pro Arg Leu Leu Asp Asp Tyr Glu Lys Ala Ala Arg His
145                 150                 155                 160

Ala Leu Lys Ala Gly Phe Asp Gly Val Gln Ile His Ala Ala Asn Gly
                165                 170                 175

Tyr Leu Ile Asp Glu Phe Ile Arg Asp Ser Thr Asn His Arg His Asp
            180                 185                 190

Glu Tyr Gly Gly Ala Val Glu Asn Arg Ile Arg Leu Leu Lys Asp Val
        195                 200                 205
```

```
Thr Glu Arg Val Ile Ala Thr Ile Gly Lys Glu Arg Thr Ala Val Arg
    210                 215                 220

Leu Ser Pro Asn Gly Glu Ile Gln Gly Thr Val Asp Ser His Pro Glu
225             230                 235                 240

Gln Val Phe Ile Pro Ala Ala Lys Met Leu Ser Asp Leu Asp Ile Ala
            245                 250                 255

Phe Leu Gly Met Arg Glu Gly Ala Val Asp Gly Thr Phe Gly Lys Thr
            260                 265                 270

Asp Gln Pro Lys Leu Ser Pro Glu Ile Arg Lys Val Phe Lys Pro Pro
        275                 280                 285

Leu Val Leu Asn Gln Asp Tyr Thr Phe Glu Thr Ala Gln Ala Ala Leu
    290                 295                 300

Asp Ser Gly Val Ala Asp Ala Ile Ser Phe Gly Arg Pro Phe Ile Gly
305             310                 315                 320

Asn Pro Asp Leu Pro Arg Arg Phe Phe Glu Lys Ala Pro Leu Thr Lys
            325                 330                 335

Asp Val Ile Glu Thr Trp Tyr Thr Gln Thr Pro Lys Gly Tyr Thr Asp
            340                 345                 350

Tyr Pro Leu Leu Gly Asp
            355
```

PROCESS FOR THE REDUCTION OF CINNAMALDEHYDE DERIVATIVE EMPLOYING ENOATE REDUCTASES

RELATED APPLICATIONS

This application is a national stage application (under 35 U.S.C. §371) of PCT/EP2011/051406, filed Feb. 1, 2011, which claims benefit of European Patent Application No. 10152321.5, filed Feb. 1, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00216_US . The size of the text file is 24 KB and the text file was created on Jul. 30, 2012.

The present invention relates to a novel enzymatically catalyzed method for the production of asymmetric aromatic aldehydes in an aqueous reaction medium containing certain organic co-solvents.

BACKGROUND OF THE INVENTION

Due to their volatility and their olfactory properties, aldehydes constitute important active ingredients in fragrance and flavour applications (a) C. Chapuis, D. Jacoby, *Appl. Catal. A: Gen.* 2001, 221, 93-117; b) D. Pybus, C. Sell, *The chemistry of fragrances*, RSC Paperbacks, Royal Society of Chemistry, Cambridge, 1999). Since the enantiomers of α- and β-substituted aldehydes often considerably differ in odour (a) A. Abate, E. Brenna, C. Fuganti, F. G. Gatti, S. Serra, *Chem. Biodivers.* 2004, 1, 1888-1898; b) L. Doszczak, P. Kraft, H.-P. Weber, R. Bertermann, A. Triller, H. Hatt, R. Tacke, *Angew. Chem. Int. Ed.* 2007, 46, 3367-3371; c) E. Brenna, C. Fuganti, S. Serra, *Tetrahedron: Asymmetry* 2003, 14, 1-42), their application in nonracemic form is often required. Whereas β-substituted aldehydes are chirally stable, α-substituted analogues are prone to racemisation, which requires sophisticated methods for their preparation. Among them, the desymmetrisation of conjugated enals via asymmetric hydrogenation is the method of choice (L. A. Saudan, *Acc. Chem. Res.* 2007, 40, 1309-1319). Whereas numerous protocols using chirally modified homogeneous (transition-metal) containing catalysts have been reported (For example see: a) S. Akutagawa, *Appl. Catal. A: Gen.* 1995, 128, 171-207; b) S. Bovo, A. Scrivanti, M. Bertoldini, V. Beghetto, O. Matteoli, *Synthesis* 2008, 2547-2550; c) W. S. Knowles, R. Noyori, *Acc. Chem. Res.* 2007, 40, 1238-1239; d) A. J. Minnaard, B. L. Fering a, L. Lefort, J. G. de Vries, *Acc. Chem. Res.* 2007, 40, 1267-1277), metal-independent organocatalysts for the reduction of enals at the expense of a nicotinamide-mimic ('Hantzsch-ester') as hydride source were developed more recently (a) J. W. Yang, M. T. H. Fonseca, N. Vignola, B. List, *Angew. Chem. Int. Ed.* 2005, 44, 108-110; b) H. Adolfsson, *Angew. Chem. Int. Ed.* 2005, 44, 3340-3342; c) S. G. Ouellet, A. M. Walji, D. W. C. MacMillan, *Acc. Chem. Res.* 2007, 40, 1327-1339; d) K. Akagawa, H. Akabane, S. Sakamoto, K. Kudo, *Tetrahedron: Asymmetry* 2009, 20, 461-466). To date, chirally surface-modified heterogeneous catalysts are not competitive (a) D. J. Watson, R. J. B. R. J. Jesudason, S. K. Beaumont, G. Kyriakou, J. W. Burton, R. M. Lambert, *J. Am. Chem. Soc.* 2009, 131, 14584-14589; b) A. Tungler, E. Sipos, V. Hada, *Curr. Org. Chem.* 2006, 10, 1569-1583). As an alternative to the variety of chemo-catalytic methods, bioreduction has been envisaged by using various types of redox enzymes (S. Serra, C. Fuganti, E. Brenna, *Trends Biotechnol.* 2005, 23, 193-198). In order to circumvent tedious protein purification and external cofactor-recycling, whole microbial cells—most prominent baker's yeast—were employed for the reduction of enals. Due to the presence of competing ene- and carbonyl-reductases, the chemo- and stereoselective bioreduction of enals was impossible, since undesired carbonyl reduction always overruled the desired C=C-bond reduction, thereby causing substrate- and product-depletion via formation of the corresponding allylic and/or saturated alcohols (a) M. Majeric, A. Avdagic, Z. Hamersak, V. Sunjic, *Biotechnol. Lett.* 1995, 17, 1189-1194; b) C. Fuganti, S. Serra, *J. Chem. Soc. Perkin Trans.* 1, 2000, 3758-3764; c) P. D'Arrigo, C. Fuganti, G. Pedrocchi-Fantoni, S. Servi, *Tetrahedron* 1998, 54, 15017-15026; d) G. Fronza, C. Fuganti, P. Grasselli, L. Majori, G. Pedrocchi-Fantoni, F. Spreafico, *J. Org. Chem.* 1982, 47, 3289-3296; e) G. Fronza, C. Fuganti, M. Pinciroli, S. Serra, *Tetrahedron: Asymmetry* 2004, 15, 3073-3077; f) V. Sunjic, M. Majeric, Z. Hamersak, *Croat. Chem. Acta* 1996, 69, 643-660).

It was only recently, that oxygen-stable ene-reductases from the Old Yellow Enzyme family became available in sufficient amounts, which allowed the chemo- and stereoselective bioreduction of activated C=C-bonds in enones and enals by leaving C=O-moieties untouched (for a review see: a) R. Stuermer, B. Hauer, M. Hall, K. Faber, *Curr. Opin. Chem. Biol.* 2007, 11, 203-213; b) S. K. Padhi, D. J. Bougioukou, J. D. Stewart, *J. Am. Chem. Soc.* 2009, 131, 3271-3280; c) J. F. Chaparro-Riggers, T. A. Rogers, E. Vazquez-Figueroa, K. M. Polizzi, A. S. Bommarius, *Adv. Synth. Catal.* 2007, 349, 1521-1531; d) M. Kataoka, A. Kotaka, R. Thiwthong, M. Wada, S, Nakamori, S. Shimizu, *J. Biotechnol.* 2004, 114, 1-9. For the stereoselective bioreduction of α-methylcinnamaldehyde see: A. Müller, B. Hauer, B. Rosche, *Biotechnol. Bioeng.* 2007, 98, 22-29). Encouraged by our recent results (a) M. Hall, C. Stueckler, W. Kroutil, P. Macheroux, K. Faber, *Angew. Chem. Int. Ed.* 2007, 46, 3934-3937; b) M. Hall, C. Stueckler, H. Ehammer, E. Pointner, G. Oberdorfer, K. Gruber, B. Hauer, R. Stuermer, W. Kroutil, P. Macheroux, K. Faber, *Adv. Synth. Catal.* 2008, 350, 411-418; c) M. Hall, C. Stueckler, B. Hauer, R. Stuermer, T. Friedrich, M. Breuer, W. Kroutil, K. Faber, *Eur. J. Org. Chem.* 2008, 1511-1516), we investigated the application of these enzymes for the preparation of nonracemic α-methyl dihydrocinnamaldehyde derivatives used in perfumery applications (for the stereoselective bioreduction of α-methylcinnamaldehyde see: A. Müller, B. Hauer, B. Rosche, *Biotechnol. Bioeng.* 2007, 98, 22-29).

There is still a need for improved enzymatic methods of preparing enantiomeric forms of alpha-substituted aromatic aldehydes.

SUMMARY OF THE INVENTION

This problem was surprisingly solved by providing an enzymatically catalyzed method as defined in the attached claims.

In particular, nonracemic aryl-substituted aldehydes, as for example α-methyldihydrocinnamaldehyde derivatives, employed as olfactory principles in perfumes (Lilial™, Helional™) were obtained according to the invention via enzymatic reduction of the corresponding precursors (i.e. cinnamaldehyde precursor) using different cloned and over-expressed ene-reductases. Whereas (R)-enantiomers were obtained using YqjM and isoenzyme OPR1 (e.e.$_{max}$ 53%), OPR3, NCR and OYEs 1-3 furnished (S)-aldehydes in up to 97% e.e. under optimised reaction conditions in presence of t-butyl methyl ether as co-solvent. The stereochemical outcome of the reduction of α-methylcinnamaldehyde using NCR and OYE1-3 [previously reported to be (R)] was unambiguously corrected to be (S).

DESCRIPTION OF THE FIGURES

FIG. 1. Dependence of reaction rate and stereoselectivity on proportion of organic co-solvent (t-BuOMe, v:v) in the reduction of 1a using OYE3.

DETAILED DESCRIPTION OF THE INVENTION

1. Specific Embodiments

The present invention, in particular, relates to the following embodiments:
1. In a first embodiment the present invention provides a biocatalytic, in particular an enzymatically catalyzed method for the production, in particular the asymmetric synthesis, of an aldehyde compound of the general formula I

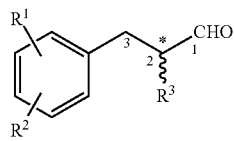

(I)

wherein
R$^1$ and R$^2$ independently of each other represent linear or branched, optionally substituted alkyl, like C$_1$-C$_8$ or C$_1$-C$_6$ alkyl; alkenyl, like C$_2$-C$_8$ or C$_2$-C$_6$ alkenyl; alkinyl, like C$_2$-C$_8$ or C$_2$-C$_6$ alkinyl; alkoxy, like C$_1$-C$_8$ or C$_1$-C$_6$ alkoxy; alkenyloxy, like C$_2$-C$_8$ or C$_2$-C$_6$ alkenyloxy; —H, —OH, —SH, -halogen, like F, Cl or Br; —NH$_2$, or —NO$_2$;
in particular, H or linear or branched alkyl, like C$_1$-C$_6$ or C$_1$-C$_4$ alkyl; alkenyl, like C$_2$-C$_6$ alkenyl; alkinyl, like C$_2$-C$_6$ alkinyl; alkoxy, like C$_1$-C$_6$ or C$_1$-C$_4$ alkoxy; alkenyloxy, like C$_2$-C$_6$ alkenyloxy; or more particular H or branched C$_3$-C$_6$ alkyl or C$_3$-C$_6$ alkenyl;
or R$^1$ and R$^2$ represent together a group of the formula —O—R$^4$—O—, wherein R$^4$ represents an optionally substituted alkylen, like C$_1$-C$_4$ alkylen or alkenylen, like C$_2$-C$_6$ or C$_3$-C$_6$ alkenylen; and
R$^3$ represents H, alkyl, like C$_1$-C$_6$ alkyl; or alkoxy, like C$_1$-C$_6$ alkoxy, in particular C$_1$-C$_4$ alkyl;
wherein said compound, if it contains an asymmetric carbon atom in position 2, is in (R) or (S) configuration;
which method comprises:
a) enzymatically reducing (in the presence or absence of molecular oxygen, i.e. aerobically or anaerobically) a compound of formula II (in particular in E-configuration),

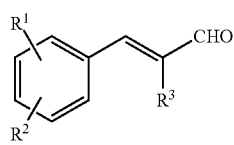

(II)

wherein
R$^1$, R$^2$ and R$^3$ are as defined above,
in an aqueous reaction medium comprising as a co-solvent at least one ether compound of the formula III

(III)

wherein
R$^5$ and R$^6$ independently of each other represent a linear or branched alkyl group; and also containing at least one reductase enzyme, in particular, capable of reducing or hydrogenating said compound of formula II at position C2/C3, catalyzing said reduction step and at least one cofactor (reduction equivalent) for said reductase;
and
b) optionally isolating said compound of formula I in the form of a substantially pure stereoisomer or as a mixture of stereoisomers.

2. The method of embodiment 1, wherein said co-solvent is selected from non-symmetric ether compounds of formula IV wherein R$^5$ and R$^6$ are different, in particular different C$_1$-C$_8$ alkyl groups.

3. The method of embodiment 2, wherein said co-solvent is selected from non-symmetric ether compounds of formula IV wherein one or the residues R$^5$ and R$^6$ is a branched alkyl group, in particular a branched C$_3$-C$_8$ alkyl (i.e. containing at least one (like 1 or 2) secondary or tertiary carbon atom) group.

4. The method of embodiment 3, wherein said co-solvent is a t-butyl alkyl ether, in particular a t-butyl C$_1$-C$_4$ alkyl ether, like t-butyl methyl ether.

5. The method of one of the preceding embodiments wherein the co-solvent is present in a proportion of 0.1 to 80, as for example 1 to 50, 5 to 40 or 10 to 30 vol.-% in the reaction medium.

6. The method of one of the preceding embodiments, wherein said reductase is selected from the group consisting of
a) OYE1 comprising an amino acid sequence of SEQ ID NO: 1, or a sequence identical to at least 50% with said SEQ ID NO: 1, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3);
b) OYE2 comprising an amino acid sequence of SEQ ID NO: 2, or a sequence identical to at least 50% with said SEQ ID NO: 2, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3);
c) OYE3 comprising an amino acid sequence of SEQ ID NO: 3, or a sequence identical to at least 50% with said SEQ ID NO: 3, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3);

d) OPR1 comprising an amino acid sequence of SEQ ID NO: 4, or a sequence identical to at least 50% with said SEQ ID NO: 4, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3);

e) OPR3 comprising an amino acid sequence of SEQ ID NO: 5, or a sequence identical to at least 50% with said SEQ ID NO: 5, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3);

f) NCR comprising an amino acid sequence of SEQ ID NO: 7, or a sequence identical to at least 50% with said SEQ ID NO: 7, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3); or g) YqjM comprising an amino acid sequence of SEQ ID NO: 6, or a sequence identical to at least 50% with said SEQ ID NO: 6, as for example at least 60, 70, 80, 85, 90, 92, 95, 96, 97, 98 or 99% sequence identity, and still retaining the intended enzyme activity (or function), i.e. being applicable as reductase enzyme, in particular as reductase capable of reducing, i.e. hydrogenating, a compound of formula II at position C2/C3 (and optionally also oxidizing, i.e. dehydrogenating, a compound of formula I at position C2/C3).

Each of said enzymes belongs to the class of enolate reductases (EC 1.3.1.X).

In particular these enzymes are or the following origin:
OPR1: *Solanum lycopersicon*
OPR3: *Solanum lycopersicon*
YqjM: *Bacillus subtilis* NamA
OYE1: *Saccharomyces carlsbergensis,*
OYE2 and OYE3: *Saccharomyces cerevisiae*
NCR: *Zymomonas mobilis*

7. The method of one of the preceding embodiments, wherein the reaction is performed in the presence of NADH or NADPH as reduction equivalent or cofactor (or the corresponding reverse reaction in the presence of NAD$^+$ or NADP$^+$).

8. The method of one of the preceding embodiments, wherein reduction reaction is coupled to a cofactor-recycling reaction, in particular an enzymatic cofactor-recycling reaction.

9. The method of embodiment 8, wherein oxidized cofactor NAD$^+$ is recycled by coupling to the glucose dehydrogenase (EC 1.1.1.47) catalyzed oxidation of glucose, thus forming gluconolactone and regenerating NADH.

10. The method of one of the preceding embodiments, wherein the enzymes involved are present in the reaction medium either in dissolved, dispersed or immobilized form.

11. The method of one of the preceding embodiments, wherein the reaction medium is buffered to a pH in the range of 6.5 to 8.5, like 7.0 to 8.0.

12. The method of one of the preceding embodiments, wherein the reaction temperature is in the range of 5 to 60, 10 to 50, or in particular 20 to 40° C.

The invention also encompasses the corresponding reverse reaction of the conversion as defined in embodiments 1 to 12, i.e. the biocatalytic oxidation (dehydrogenation) of a compound of formula I to a compound of formula II.

2. Explanation of Particular Terms

Unless otherwise stated the following meanings shall apply:

The term "biocatalytic" or "enzymatically catalyzed" method refers to any method performed in the presence of catalytic activity of an enzyme as defined herein, i.e. in the presence of isolated pure or crude enzyme or entire microbial cells containing or expression such enzyme activity.

The term "stereospecific" means that one out of several stereoisomers or enantiomers is formed by the enzyme in high enantiomeric excess or purity, of at least 90% ee, preferably at least 95% ee, in particular at least 98% ee, or at least 99% ee. the ee % value is calculated according to the following formula $$ee\% = [X_A - X_B]/[X_A + X_B]*100,$$

wherein $X_A$ and $X_B$ refer to the molar fraction of enantiomer A or B, respectively.

Examples of "stereoisomers" are E- and Z-isomers or, in particular R- and S-enantiomers.

The term "substantially pure" is meant to describe a molecule, which is homogeneous by one or more purity or homogeneity characteristics used by those of skill in the art.

A "substantially pure" protein or enzyme means that the desired purified protein is essentially free from contaminating cellular components, as evidenced by a single band following polyacrylamide-sodium dodecyl sulfate gel electrophoresis (SDS-PAGE). A "substantially pure" enzyme or protein will show constant and reproducible characteristics within standard experimental deviations for parameters such as the following: molecular mass, chromatographic migration, amino acid composition, amino acid sequence, blocked or unblocked N-terminus, HPLC elution profile, biological activity, and other such parameters. For example, a "substantially pure" protein or enzyme means that the desired purified protein is essentially free from contaminating cellular components, as evidenced by a single band following polyacrylamide-sodium dodecyl sulfate gel electrophoresis (SDS-PAGE). The term, however, is not meant to exclude artificial or synthetic mixtures of said enzyme or protein with other compounds. In addition, the term is not meant to exclude fusion proteins optionally isolated from a recombinant host.

Within chemical compounds of formulae I, II and III the following meanings shall apply:

Alkyl as well as alkyl fragment of residues derived there from, as for example alkoxy, represent saturated, linear or branched hydrocarbon chains having 1 to 4, 1 to 6, 1 to 8, or 1 to 10 carbon atoms, like $C_1$-$C_6$-Alkyl like methyl, ethyl, propyl, 1-methylethyl, butyl, 1-methyl-propyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_6$-Alkoxy, like $C_1$-$C_4$-alkoxy, as for example methoxy, ethoxy, n-propoxy, 1-methylethoxy, butoxy, 1-methylpropoxy, 2-methylpropoxy or 1,1-dimethylethoxy; as well as e.g. pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

Alkenyl: one-fold or multipe, in particular one-fold non-saturated, straight-chain or branched hydrocarbon residues having 2 to 4, 2 to 6, 2 to 8, or 2 to 10 carbon atoms and a double bond in any position, like $C_2$-$C_6$-alkenyl, as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkenyloxy: oxygen-linked analogs of the above alkenyl groups, like corresponding $C_2$-$C_6$-alkenyloxy groups.

Alkinyl: analogs of the above alkenyl groups wherein a carbon-carbon double bond is replaced by a triple bond.

Alkylen: straight chain or branched hydrocarbon bridges having up to 7 carbon atoms, as for example $C_1$-$C_7$-alkylen groups like —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—, —$(CH_2)_4$—, —$(CH_2)_5$—, —$(CH_2)_6$, —$(CH_2)_7$—, —$CH(CH_3)$—$CH_2$—$CH_2$—$CH(CH_3)$— or —$CH(CH_3)$—$CH_2$—$CH_2$—$CH_2$—$CH(CH_3)$— or $C_1$-$C_4$-alkylen groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$.

Alkenylen: represent the one-fold or multiply, in particular, one-fold non-saturated, analogues of the above alkylen groups, having 2 to 8 carbon atoms, in particular $C_2$-$C_7$-alkenylenes or $C_2$-$C_4$-alkenylenes, like —CH═CH—, —CH═CH—$CH_2$—, —$CH_2$—CH═CH—, —CH═CH—$CH_2$—$CH_2$—, —$CH_2$—CH═CH— $CH_2$—, —$CH_2$—$CH_2$—CH═CH—, —$CH(CH_3)$—CH═CH—, —$CH_2$—$C(CH_3)$═CH—.

Optional substituents may be selected from —COOH, —COO-alkyl, —OH, —SH, —CN, amino, —$NO_2$, alkyl, or alkenyl, alkyl or alkenyl being as defined above.

3. Further Embodiments of the Invention 3.1 Proteins According to the Invention

The present invention is not limited to the specifically mentioned enzymes/proteins, but also extends to functional equivalents thereof.

"Functional equivalents" or "analogs" or "functional mutations" of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more, like 1 to 20, 1 to 15, 1 to 10 or 1 to 5, amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448.

The percent identity values may also be calculated from BLAST alignments, algorithm blastp (protein-protein BLAST) or by applying the Clustal setting as given below. Typical percent identity values are for example in the range of 50% or more, as for example at least 60, 70, 80, 85, 90, 91, 92, 93, 94, 95, 96, 97, 98 or 99%.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

3.2 Coding Nucleic Acid Sequences

The invention also relates to nucleic acid sequences that code for enzymes/proteins as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| FAST algorithm | on |
|---|---|
| K-tuplesize | 1 |
| Gap penalty | 3 |
| Window size | 5 |
| Number of best diagonals | 5 |

Alternatively the identity may be determined according to Chema, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| DNA Gap Open Penalty | 15.0 |
|---|---|
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E.F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

3.3 Preparation of Functional Mutants

The skilled reader is also aware of methods of generating functional mutants.

Depending on the technique applied, a skilled reader may generate arbitrary or directed mutations in genes or noncoding nucleic acid regions (which, for example, may be of importance for regulating gene expression) and, afterwards, may generate suitable gene libraries. The molecular biological method required therefore all well known in the art, and, for example, described by Sambrook and Russell, Molecular Cloning. 3. Edition, Cold Spring Harbor Laboratory Press 2001.

Methods of modifying genes and consequently of modifying the encoded proteins are well known to the skilled reader, as for example site-specific mutagenesis wherein single or multiple nucleotides of a gene are specifically replaced (Trower M K (Ed.) 1996; In vitro mutagenesis protocols. Humana Press, New Jersey), saturation mutagenesis, wherein at any position of a gene the codon of any amino acid may be exchanged or added (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1), error-prone polymerase chain reaction (PCR), wherein nucleotide sequences are mutated via the action of an incorrectly functioning DNA-polymerase (Eckert K A, Kunkel T A (1990) Nucleic Acids Res 18:3739);

SeSaM method (Sequence Saturation Method), wherein preferred substitutions are avoided by the polymerase (Schenk et al., Biospektrum, Vol. 3, 2006, 277-279)

Passaging of genes in mutator-strains, showing an increased occurrence of mutations of nucleotide sequences, for example in view of a defective DNA-repair mechanism (Greener A, Callahan M, Jerpseth B (1996) An efficient random mutagenesis technique using an E. coli mutator strain. In: Trower M K (Hrsg.) In vitro mutagenesis protocols. Humana Press, New Jersey), or DNA-Shuffling, wherein a pool of closely related genes is formed and digested and wherein the fragments are used as templates for a PCR reaction, and wherein full-length mosaic genes are formed (Stemmer W P C (1994) Nature 370:389; Stemmer W P C (1994) Proc Natl Acad Sci USA 91:10747).

By applying the so-called directed evolution technique (see for example Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Hrsg.) Manual of industrial microbiology and biotechnology.

American Society for Microbiology) a skilled reader will be able to specifically prepare functional mutants in large scale. In a first step libraries of a specific protein are generated, for example, by applying any one of the above mentioned methods. Afterwards said libraries are expressed, for example by applying bacteria or phage display systems.

Those genes expressing functional mutants showing the desired feature profile may be selected and subjected to further mutation. The steps of mutation and selection or screening may be repeated iteratively until one of the obtained mutants shows the desired feature profile.

By the iterative approach a limited number of mutations, as for example 1 to 5 mutations, may be performed and their influence on the enzyme feature at issue may be evaluated and further improved mutants may be selected stepwise. Said selected mutant may then be subjected to a further mutation in substantially the same may. The number of single mutants to be evaluated may be reduced significantly in this way.

The teaching of the present invention provide important information as regards structure and sequence of the enzyme/protein at issue, based on which it should be possible to generate further enzymes/proteins with the desired modified feature profile. In particular, so-called hot spots, i.e. sequence regions may be defined, which potentially may be suited for further mutation in order to modify or generate a desired feature of the enzyme/protein.

3.4 Constructs Used According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, lacI$^{q-}$, T7-, T5-, T3-, gal-, trc-, ara-, rhaP (rhaP$_{BAD}$) SP6-, lambda-P$_R$- or in the lambda-P$_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl; in nocardioform actinomycetes pJAM2; in *Streptomyces* pIJ101, pIJ364, pIJ702 or pIJ361; in *bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018). Further suitable plasmids are also mentioned in the experimental part.

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-New York-Oxford, 1985).

3.5 Hosts that can be Used According to the Invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for the fermentative production according to the invention.

Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

The host organism or host organisms according to the invention preferably contain at least one of the nucleic acid sequences, nucleic acid constructs or vectors described in this invention, which code for an enzyme activity according to the above definition.

3.6 Enzymatic Production of Products of the Invention

An aliquot of at least one reductase enzyme is provided in dissolved or dispersed, for example immobilized form, in a proper protein concentration for performing the biotransformations, as for example in the range of 10 to 300 or 75 to 125 µg/ml. The reaction is typically performed in buffered reaction medium containing a suitable buffer, as for example Tris-HCl buffer (for example 0.01 to 0.1 M) containing the substrate in a suitable concentration (about 0.1 to 100 mM) and the cofactor (NADH) (in a proper concentration range, like 0.1 to 100 mM). The organic co-solvent may be added in a suitable proportion of from 0.1 to 80 vol.-%. Optionally the substrate may be pre-dissolved in the organic co-solvent and the be added to the aqueous medium. The reaction mixture may be agitated or shaken at a suitable intensity, at a suitable temperature in the range of 10 to 50 like 25 to at 30° C. for a suitable period of time. After sufficient reaction time, as for example 1 to 120 h or 10 to 24 h the products may be extracted, for example EtOAc. Other suitable extractants are well known to a skilled reader.

For cofactor-recycling an aliquot of required enzyme, i.p. glucose dehydrogenase, may be added to the reaction mixture, in dissolved or dispersed, as for example immobilized form and at a suitable proportion (for example in range of 1 to 50 or 5 to 15 or 10 µml) together with the co-substrate (like glucose) also in proper concentration (like 0.1 to 100 mM) to drive the recycling reaction, which is preferably coupled to the principal reductase reaction.

3.7 Fermentative Production of Products of the Invention

The invention also relates to methods for the fermentative production of compounds of formula (I).

The recombinant microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

3.8 Enzyme Immobilization

If an enzyme as sued according to the invention, is immobilised, it is attached to an inert carrier. Suitable carrier materials are known in the art and are, e.g., disclosed in EP-A-1149849, EP-A-1 069 183 and DE-OS 100193773 as well as the literature references cited therein (all of which are specifically enclosed with regard to carrier materials). Examples for suitable carrier materials are clays, clay minerals such as kaolinite, diatomeceous erth, perlite, silica, alumina, sodium carbonate, calcium carbonate, cellulose powder, anion exchanger materials, synthetic polymers, such as polystyrene, acrylic resins, phenol formaldehyde resins, polyurethanes and polyolefines, such as polyethylene and polypropylene. For preparing carrier-bound enzymes the carrier materials usually are used in the form of fine powders, wherein porous forms are preferred. The particle size of the carrier material usually does not exceed 5 mm, in particular 2 mm. In case the at least one enzyme is present in a whole-cell-preparation, said whole-cell-preparation may be present in a free or immobilised form. Suitable carrier materials are e.g. Ca-alginate or Carrageenan. Enzymes as well as cells may directly be linked by glutaraldehyde. A wide range of immobilisation methods is known in the art (e.g. J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim).

3.9 Product Isolation

The methodology of the present invention can further include a step of recovering compounds as produced according to the invention. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

EXPERIMENTAL PART

Unless otherwise stated the following experiments have been performed by applying standard equipment, methods, chemicals, and biochemicals as used in genetic engineering, fermentative production of chemical compounds by cultivation of microorganisms and in the analysis and isolation of products. See also Sambrook et al, and Chmiel et al as cited herein above.

Materials and Methods a) General Methods

TLC plates were run on silica gel Merck 60 ($F_{254}$) and compounds were visualized by spraying with Mo-reagent [$(NH_4)_6Mo_7O_{24}.4H_2O$ (100 g/L), $Ce(SO_4)_2.4H_2O$ (4 g/L) in $H_2SO_4$ (10%)] or by UV (254 nm).

Conversion and enantiomeric excess were determined via GC or HPLC analysis, respectively.

GC analysis was carried out on a Varian 3800 gas chromatograph equipped with a FID detector using $H_2$ as carrier gas (14.5 psi), using an achiral stationary phase [for the determination of conversion (Varian CP-1301, 6% cyanopropylphenyl phase capillary column, 30 m, 0.25 mm, 0.25 μm), column A] or a chiral stationary phase [for the determination of the enantiomeric excess (Hydrodex-β-6TBDM, modified β-cyclodextrin capillary column, 25 m×0.25 mm), column B]. Temperature of the injector and detector were 180 and 250° C., respectively, using a split ratio of 20:1.

Chiral HPLC analyses were carried out on a Shimadzu system equipped with a Chiralcel OD-H column (column C, 0.46×25 cm) or a Chiralcel OJ column (column D, 0.46×25 cm) for the determination of the enantiomeric excess.

NMR spectra were measured in $CDCl_3$ using a Bruker AMX spectrometer at 360 ($^1H$) and 90 ($^{13}C$) MHz. Chemical shifts are reported relative to TMS (☐0.00) and coupling constants (J) are given in Hz. Optical rotation values ($[\alpha]_D^{20}$) were measured on a Perkin-Elmer polarimeter 341 at 589 nm (Na-line) in a 1 dm cuvette and are given in units of [(deg× mL)/(g×dm)].

Protein concentrations were determined using the Bio-Rad microassay with bovine serum albumin as standard. SDS-PAGE was done in a Mini Protein apparatus (Bio-Rad, Heidelberg, Germany). Proteins were stained with Coomassie brilliant blue (Serva, Heidelberg, Germany).

b) Materials

NADH and $NAD^+$ were purchased from Biocatalytix/Codexis, glucose was obtained from Fluka and glucose dehydrogenase from Julich Chiral Solutions.

(E)-3-(4-tert-Butylphenyl)-2-methylpropenal (1a), (E)-3-(1,3-benzodioxole-5-yl)-2-methylpropenal (2a) and (E)-α-methylcinnamaldehyde (3a) were provided by BASF (Ludwigshafen).

(E)-3-(4-tert-Butylphenyl)-2-methylpropenal (1a): $^1H$ (360 MHz, $CDCl_3$) δ=1.37 (s, 9H), 2.11 (s, 3H), 7.27 (s, 1H) 7.48-7.53 (m, 4H), 9.59 (s, CHO); $^{13}C$ (90 MHz, $CDCl_3$) δ=10.96, 31.15, 34.89, 125.72, 130.07, 149.96, 195.70.

(E)-3-(1,3-Benzodioxole-5-yl)-2-methylpropenal (2a): $^1H$ (360 MHz, $CDCl_3$) δ=2.07 (s, 3H), 6.05 (s, 2H), 6.9-7.08 (m, 3H) 7.16 (s, 1H), 9.53 (s, 1H); $^{13}C$ (90 MHz, $CDCl_3$) δ=10.95, 101.62, 108.65, 109.62, 125.81, 129.44, 136.58, 148.09, 148.88, 149.75, 195.40.

(E)-α-Methylcinnamaldehyde (3a): $^1H$ (360 MHz, $CDCl_3$) δ=2.10 (s, 3H), 7.28 (s, 1H), 7.39-7.56 (m, 5H), 9.61 (s, CHO); $^{13}C$ (90 MHz, $CDCl_3$) δ=10.94, 128.72, 129.57, 130.03, 135.16, 138.39, 149.80, 195.55.

c) Cloning of Genes

Routine manipulation of DNA, PCR and construction of recombinant plasmids were performed as described in (Sambrook J & Russell D W (2001) Molecular Cloning: a Laboratory Manual, 3$^{rd}$ edn. Cold Spring. Harbor Laboratory Press, Cold Spring Harbor, N.Y.).

The open reading frame of *Lycopersicon esculentum* OPR1 was cloned into pET-21a and overexpressed as a C-terminal hexahistidine tagged protein in *E. coli* BL21 cells (C. Breithaupt, J. Strassner, U. Breitinger, R. Huber, P. Macheroux, A. Schaller, T. Clausen, Structure, 2001, 9, 419-429). The overexpressed recombinant protein was purified on a Ni-NTA affinity column (Invitrogen) according to the manufacturer's protocol. *Lycopersicon esculentum* OPR3 and YqjM from *Bacillus subtilis* were overexpressed and purified as reported recently (C. Breithaupt, R. Kurzbauer, H. Lilie, A. Schaller, J. Strassner, R. Huber, P. Macheroux, T. Clausen, *Proc. Natl. Acad. Sci. USA* 2006, 103, 14337-14342; K. Kitzing, T. B. Fitzpatrick, C. Wilken, J. Sawa, G. P. Bourenkov, P. Macheroux, T. Clausen, *J. Biol. Chem.* 2005, 280, 27904-27913)

The cloning, purification and characterisation of old yellow iso-enzymes from yeast (OYE1 from *Saccharomyces carlsbergensis*, OYE2 and OYE3 from *Saccharomyces cerevisiae*) and *Zymomonas mobilis* reductase (NCR) were performed according to literature (A. Müller, B. Hauer, B. Rosche, *Biotechnol. Bioeng.* 2007, 98, 22-29; K. Saito, D. J. Thiele, M. Davio, O. Lockridge, V. Massey, *J. Biol. Chem.* 1991, 266, 20720-20724; K. Stott, K. Saito, D. J. Thiele, V. Massey, *J. Biol. Chem.* 1993, 268, 6097-6106; Y. S, Niino, S. Chakraborty, B. J. Brown, V. Massey, *J. Biol. Chem.* 1995, 270, 1983-1991).

NEM-reductase (from *E. coli*), PETN-reductase (from *Enterobacter cloacae*) and morphinone-reductase (from *Pseudomonas putida* M10) were provided by N. C. Bruce (Department of Biology, University of York, York, UK) a) C. E. French, S, Nicklin, N. C. Bruce, *J. Bacteriol.* 1996, 178, 6623-6627; b) K. Miura, Y. Tomioka, H. Suzuki, M. Yonezawa, T. Hishinuma, M. Mizugaki, *Biol. Pharm. Bull.* 1997, 20, 110-112; c) C. E. French, N. C. Bruce, *Biochem. J.* 1994, 301, 97-103.

Example 1

Synthesis of Reference Materials Via Catalytic Hydrogenation (E)-Alkene (1a-3a, 0.5 mmol) was dissolved in THF (10 mL) and hydrogenated under $H_2$ at atmospheric pressure and at room temperature employing Pd/C (10%, 5 mg) as catalyst. After the mixture was stirred overnight at room temperature, the reaction mixture was filtered through Celite and concentrated to yield racemic reference materials (rac-1b-3b) at 99% conversion. Thus were obtained:

rac-3-(4-tert-Butylphenyl)-2-methylpropanal (Lysmeral™, Lilial™, rac-1 b): $^1H$ (360 MHz, $CDCl_3$) δ=1.11-1.12 (d, 3H, J=6.8 Hz), 1.33 (s, 9H), 2.59-2.63 (m, 2H), 3.05-3.09 (m, 1H), 7.11-7.13 (d, 2H, J=8.2), 7.32-7.35 (d, 2H, J=8.2), 9.74-9.75 (d, CHO, J=1.4); $^{13}C$ (90 MHz, $CDCl_3$) δ=13.30, 31.37, 34.39, 36.16, 48.02, 125.41, 128.67, 204.62.

rac-3-(1,3-Benzodioxole-5-yl)-2-methylpropanal (Tropional™, Helional™, rac-2b): $^1H$ (360 MHz, $CDCl_3$) δ=1.09-1.11 (d, 3H, J=6.8), 2.52-2.66 (m, 2H), 2.99-3.04 (m, 1H), 5.95 (s, 2H), 6.62-6.76 (m, 3H) 9.72 (s, CHO); $^{13}C$ (90 MHz, $CDCl_3$) δ=13.18, 36.40, 48.22, 100.91, 108.25, 109.30, 121.94, 132.50, 146.11, 147.73, 204.41.

rac-2-Methyl-3-phenylpropanal (rac-3b): $^1$H (360 MHz, CDCl$_3$) δ=1.10-1.12 (d, 3H, J=6.8 Hz), 2.59-2.73 (m, 2H), 3.09-3.14 (m, 1H), 7.18-7.34 (m, 5H), 9.74-9.75 (d, CHO, J=1.3 Hz); $^{13}$C (90 MHz, CDCl$_3$) δ=13.21, 36.65, 48.04, 126.42, 128.53, 129.02, 138.83, 204.39.

Example 2

Bioreduction Experiments with Different Cinnamaldehydes

Scheme 1

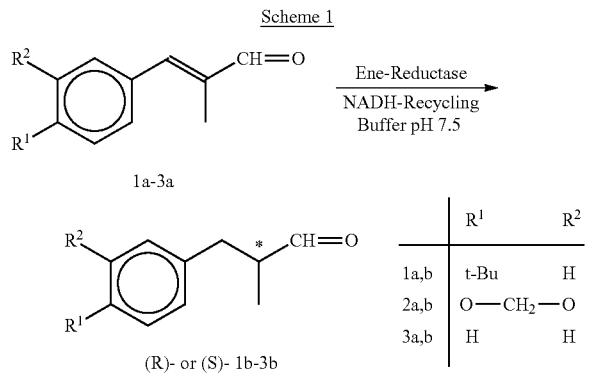

Asymmetric bioreduction of α-methylcinnamaldehyde derivatives 1a-3a.

2.1 Preparation Experiments (1) General Procedure for the Enzymatic Bioreduction Under Standard Conditions An aliquot of enzyme (OPR1, OPR3, YqjM, OYE1-3, NCR, NEM-reductase, protein concentration in biotransformations: 75-125 µg/mL) was added to a Tris-HCl buffer solution (0.8 mL, 50 mM, pH 7.5) containing the substrate (10 mM) and the cofactor NADH (10 mM). The mixture was shaken at 30° C. and 120 rpm. After 24 h the products were extracted with EtOAc (2×0.5 mL). The combined organic phases were dried over Na$_2$SO$_4$ and analysed on achiral GC to determine the conversion and on chiral GC or HPLC, respectively, to determine the enantiomeric excess.

(2) General Procedure for Cofactor Recycling

An aliquot of enzyme (see above) was added to a Tris-HCl buffer solution (0.8 mL, 50 mM, pH 7.5) containing the substrate (10 mM) the oxidized form of the cofactor (NAD$^+$, 100 µM), the cosubstrate (glucose, 20 mM) and the recycling enzyme (glucose dehydrogenase, 10 U). The mixture was shaken at 30° C. and 120 rpm for 24 h and worked up as described above.

(3) General Procedure for the Enzymatic Bioreduction Using Organic Cosolvents

An organic co-solvent (EtOH, i-Pr$_2$O, tert-BuOMe, ethyl acetate and n-hexane) was employed in a ratio of 20% (v:v). The substrate (10 mM) was dissolved in the organic solvent (200 µL, for the cosolvent concentration study in 50-250 µL of t-BuOMe) and added to a Tris-HCl buffer solution (0.75-0.95 mL, 50 mM, pH 7.5) containing either the cofactor NADH (10 mM) or the cofactor recycling system (see above) followed by the addition of an aliquot of enzyme (see above). The mixture was shaken at 30° C. and 120 rpm for 24 h and worked up as described above.

2.2 Analytical Experiments (1) Determination of the Absolute Configuration.

The absolute configuration of the products 1b-3b was determined by comparison of its optical rotation value ($[α]_D^{20}$) with literature data. The absolute configuration of 3b was independently double-checked by comparison of the optical rotation value of 3c (2-methyl-3-phenylpropan-1-ol), which was obtained by chemical reduction of 3b (derived via bioreduction of 3a using OYE2) using NaBH$_4$.

TABLE 2

Optical rotation values of products.

| Compound | $[α]_D^{20}$ | Conditions[a] | E.e. [%] | Config. | Reference |
|---|---|---|---|---|---|
| 1b[b] | +4.5 | c = 1.8, CHCl$_3$ | 83 | (S) | this study |
| 1b | −5.2 | c = 1, CHCl$_3$ | 95 | (R) | (1) |
| 2b[b] | −2.9 | c = 2.2, CHCl$_3$ | 95 | (S) | this study |
| 2b | −2.8 | c = 1.07, CHCl$_3$ | ≥90 | (S) | (2) |
| 3b[b] | −4.1 | c = 0.5, MeOH | 96 | (S) | this study |
| 3b | +7.0 | c = 0.7, MeOH | 76 | (R) | (3) |
| 3b | −4.42 | c = 4, MeOH | 94 | (S) | (4) |
| 3c[c] | −11.3 | c = 1.0, CHCl$_3$ | 96 | (S) | this study |
| 3c | −14.0 | c = 0.25, CHCl$_3$ | 87 | (S) | (5) |

[a]Concentration [g/100 mL];
[b]obtained by using OYE2;
[c]2-methyl-3-phenyl 1-propanol.
(1) D. Enders, H. Dyker, *Liebigs Ann. Chem.* 1990, 1107-1110.
(2) D. Enders, M. Backes, *Tetrahedron: Asymmetry* 2004, 15, 1813-1817.
(3) A. Baeza, C. Najera, J. M. Sansano, *Eur. J. Org. Chem.* 2007, 7, 1101-1112.
(4) M. V. Rangaishenvi, B. Singaram, H. C. Brown, *J. Org. Chem.* 1991, 56, 3286-3294.
(5) S. D. Bull, S. G. Davies, R. L. Nicholson, H. J. Sanganee, A. D. Smith, *Org. Biomol. Chem.* 2003, 1, 2886-2899.

(2) Determination of Conversion and Enantiomeric Excess.

The conversion and enantiomeric excess were determined via GC or HPLC analysis, respectively.

TABLE 3

Determination of conversion via achiral GC-analyses.

| | | | $t_R$ [min] | |
| Compound | Column[a] | Conditions[b] | 1a-3a | 1b-3b |
|---|---|---|---|---|
| 1 | A | E | 8.23 | 5.45 |
| 2 | A | E | 8.99 | 5.78 |
| 3[(f)] | A | E | 3.80 | 3.10 |

[a]Column: A = Varian CP-1301, 6% cyanopropyl-phenyl phase capillary column;
[b]conditions: E = 14.5 psi H$_2$ at 180° C., hold for 11 min.
(f)A. Scrivanti, M. Bertoldini, V. Beghetto, U. Matteoli, *Tetrahedron* 2008, 64, 543-548.

TABLE 4

Determination of enantiomeric excess via chiral GC- and HPLC-analyses.

| | | | $t_R$ [min] | |
| Compound | Column[a] | Conditions[b] | (R) | (S) |
|---|---|---|---|---|
| 1b | C | G | 29.45 | 29.73 |
| 2b | D | H | 12.5 | 13.5 |
| 3b | B | F | 11.8 | 12.7 |

[a]Column: B = Chiralcel OJ column (HPLC); C = Hydrodex-β-6TBDM, modified β-cyclodextrin capillary column (GC); D = Chiralcel OD-H column (HPLC);
[b]conditions: F = n-heptane/i-propanol 99:1 (isocratic) at 18° C., flow 1 mL/min, ε = 190 nm, 205 nm, 215 nm; G = 14.5 psi H$_2$ at 130° C., hold for 0 min, heat rate 1° C./min to 165° C., heat rate 20° C./min to 180° C., hold for 7 min; H = n-heptane/i-propanol 98:2 (isocratic) at 18° C. 0-15 min: flow 1 mL/min, 15-20 min: flow 1.5 mL/min, ε = 205 nm, 235 nm, 285 nm.

2.3 Results and Discussion

The reduction product of p-tert-butylcinnamaldehyde (1b) is the olfactory principle of the lily-of-the-valley (Brenna, C. Fuganti, S. Serra, *Tetrahedron: Asymmetry* 2003, 14, 1-42; A. Scrivanti, M. Bertoldini, V. Beghetto, U. Matteoli, *Tetrahedron* 2008, 64, 543-548) and is marketed under the trade name Lilial™ or Lysmeral™, whereas the m,p-methylenedioxy aldehyde 2b is the active ingredient of various perfumes and is marketed as Helional™ or Tropional™ (D. Enders, M. Backes, *Tetrahedron: Asymmetry* 2004, 15, 1813-1817. C. Chapuis, D. Jacoby, *Appl. Catal. A: Gen.* 2001, 221, 93-117; D. Pybus, C. Sell, *The chemistry of fragrances*, RSC Paperbacks, Royal Society of Chemistry, Cambridge, 1999).

The bioreduction of 1a under standard conditions in neat aqueous buffer pH 7.5 proved to be disappointingly slow using a variety of ene-reductases (data not shown). However, when the solubility of the lipophilic substrate was enhanced by addition of a small amount of di-isopropyl ether (5%, v:v), reaction rates picked up markedly (Table 5, entries 1-7). Among all enzymes, YqjM and isoenzyme OPR1 gave (R)-1b, albeit in low enantiomeric excess (e.e.$_{max}$ 21%). In contrast, OPR3, NCR and OYEs 1-3 furnished (S)-1b with slightly enhanced stereoselectivities, but they still were insufficient for synthetic purposes (e.e.$_{max}$ 64%). Since the co-solvent seemed to have a strong influence on the reaction rate, we anticipated that it might also have an impact on the stereoselectivity of the ene-reductases. An increased amount of di-isopropyl ether (20%, v:v) caused a drop in reaction rates, without altering the stereoselectivities significantly, similar effects (reduced rates and slightly diminished stereoselectivities) were observed when i-Pr$_2$O was replaced with ethyl acetate or n-hexane (20%, v:v, data not shown). A switch to the water-miscible co-solvent ethanol (20%, v:v) enhanced the rates (c$_{max}$ 80%) for OPR1, NCR and OYEs 1-3 going in hand with a decrease of stereoselectivities (e.e.$_{max}$ 51%, entries 8-12). YqjM and OPR3 were marginally active (data not shown). Finally, a switch to t-butyl methyl ether provided an ideal solution: Excellent stereoselectivities were obtained with OYEs 1-3 with a modest drop in reaction rates (e.e.$_{max}$>95%, entries 13-19).

In order to tune the system, 1a was reduced using OYE3 at increasing proportions of t-butyl methyl ether. As may be deduced from FIG. 1, a clear inverse correlation between reaction rate and stereoselectivity (plotted as conversion versus e.e.) was observed at increasing amounts of co-solvent. Overall, a fraction of 20% (v:v) of t-BuOMe seemed to be a good compromise between a decrease of activity and an increase of stereoselectivity. Consequently, all further studies were performed at this co-solvent ratio.

Under optimised conditions, 2a was accepted by all ene-reductases (entries 20-26). In line with previous observations, YqjM and OPR1 showed a low preference to furnish (R)-2b. Excellent stereoselectivities (e.e.$_{max}$ 96%) and rates (up to full conversion) were obtained with NCR and OYEs 1-3 for (S)-2b. Interestingly, the structurally and mechanistically closely related OYE-homologs N-ethylmaleimide-(NEM)-reductase, morphinone reductase and pentaerythritol tetranitrate-(PETN)-reductase showed insufficient stereoselectivities or activities, only NEM-reductase furnished (S)-1b and (S)-2b with e.e.$_{max}$ 57% and 18%, respectively (PETN-reductase gave (R)-3b with e.e.$_{max}$ 14%).

TABLE 5

Conversion and enantiomeric excess of bioreduction products 1b-3b.

| Entry | Substrate | Enzyme[a] | Conditions | Conv. Product [%] | E.e. [%] |
|---|---|---|---|---|---|
| 1 | 1a | YqjM | buffer/i-Pr$_2$O (95:5) | 3 | 13 (R) |
| 2 | 1a | OPR1 | buffer/i-Pr$_2$O (95:5) | 37 | 21 (R) |
| 3 | 1a | OPR3 | buffer/i-Pr$_2$O (95:5) | 4 | 22 (S) |
| 4 | 1a | NCR | buffer/i-Pr$_2$O (95:5) | 66 | 59 (S) |
| 5 | 1a | OYE1 | buffer/i-Pr$_2$O (95:5) | 48 | 52 (S) |
| 6 | 1a | OYE2 | buffer/i-Pr$_2$O (95:5) | 75 | 64 (S) |
| 7 | 1a | OYE3 | buffer/i-Pr$_2$O (95:5) | 67 | 64 (S) |
| 8 | 1a | OPR1 | buffer/EtOH (80:20) | 62 | 21 (R) |
| 9 | 1a | NCR | buffer/EtOH (80:20) | 68 | 40 (S) |
| 10 | 1a | OYE1 | buffer/EtOH (80:20) | 61 | 33 (S) |
| 11 | 1a | OYE2 | buffer/EtOH (80:20) | 80 | 51 (S) |
| 12 | 1a | OYE3 | buffer/EtOH (80:20) | 75 | 50 (S) |
| 13 | 1a | YqjM | buffer/t-BuOMe (80:20) | 0 | n.d. |
| 14 | 1a | OPR1 | buffer/t-BuOMe (80:20) | 3 | 17 (R) |
| 15 | 1a | OPR3 | buffer/t-BuOMe (80:20) | 0 | n.d. |
| 16 | 1a | NCR | buffer/t-BuOMe (80:20) | 26 | 83 (S) |
| 17 | 1a | OYE1 | buffer/t-BuOMe (80:20) | 26 | >95 (S) |
| 18 | 1a | OYE2 | buffer/t-BuOMe (80:20) | 26 | >95 (S) |
| 19 | 1a | OYE3 | buffer/t-BuOMe (80:20) | 42 | >95 (S) |
| 20 | 2a | YqjM | buffer/t-BuOMe (80:20) | 10 | 13 (R) |
| 21 | 2a | OPR1 | buffer/t-BuOMe (80:20) | 78 | 6 (R) |
| 22 | 2a | OPR3 | buffer/t-BuOMe (80:20) | 8 | 34 (S) |
| 23 | 2a | NCR | buffer/t-BuOMe (80:20) | 86 | 88 (S) |
| 24 | 2a | OYE1 | buffer/t-BuOMe (80:20) | 59 | 95 (S) |
| 25 | 2a | OYE2 | buffer/t-BuOMe (80:20) | >99 | 97 (S) |
| 26 | 2a | OYE3 | buffer/t-BuOMe (80:20) | 72 | 96 (S) |
| 27 | 3a | YqjM | buffer/t-BuOMe (80:20) | 26 | 33 (R) |
| 28 | 3a | OPR1 | buffer/t-BuOMe (80:20) | >99 | 53 (R) |
| 29 | 3a | OPR3 | buffer/t-BuOMe (80:20) | 22 | 28 (S) |
| 30 | 3a | NCR | buffer/t-BuOMe (80:20) | >99 | 76 (S) |
| 31 | 3a | OYE1 | buffer/t-BuOMe (80:20) | >99 | 94 (S) |
| 32 | 3a | OYE2 | buffer/t-BuOMe (80:20) | >99 | 96 (S) |
| 33 | 3a | OYE3 | buffer/t-BuOMe (80:20) | 84 | 90 (S) |

[a]YqjM = Old Yellow Enzyme homolog from *Bacillus subtilis* (a) C. E. French, S. Nicklin, N. C. Bruce, *J. Bacteriol.* 1996, 178, 6623-6627; b) K. Miura, Y. Tomioka, H. Suzuki, M. Yonezawa, T. Hishinuma, M. Mizugaki, *Biol. Pharm. Bull.* 1997, 20, 110-112; c) C. E. French, N. C. Bruce, *Biochem. J.* 1994, 301, 97-103); OPR1 and OPR3 = 12-oxophytodienoic acid reductase isoenzymes from *Lycopersicon escultentum* (tomato) (D. Enders, H. Dyker, *Liebigs Ann. Chem.* 1990, 1107-1110.); NCR = nicotinamide-dependent cyclohexanone reductase from *Zymomonas mobilis* (For the stereoselective bioreduction of α-methylcinnamaldehyde see: A. Müller, B. Hauer, B. Rosche, *Biotechnol. Bioeng.* 2007, 98, 22-29.); OYE = Old Yellow Enzymes from *Saccharomyces carlsbergensis* (OYE1) and from *S. cerevisiae* (OYE2, OYE3) (D. Enders, M. Backes, *Tetrahedron: Asymmetry* 2004, 15, 1813-1817).

The absolute configuration of products 1b and 2b was deduced by comparison of optical rotation values of 1b and 2b obtained using OYE2 with literature data (for details see experimental part), which proved to be (S) for both substrates. However, the pronounced stereochemical preference of NCR and OYEs 1-3 to yield (S)-1b and (S)-2b is in conflict with the (R)-preference of these enzymes on the close homolog □-methyldihydrocinnamaldehyde (3a), as reported by B. Rosche et al. (A. Müller, B. Hauer, B. Rosche, *Biotechnol. Bioeng.* 2007, 98, 22-29)]. According to this report, the bioreduction of 3a furnished (R)-3b in 50% and ca. 75% e.e. using NCR and OYEs 1-3, resp. In order to clarify this discrepancy, we re-investigated substrate 3a using all ene-reductases (entries 27-33). Again, the absolute configuration of 3b obtained by using OYE2 was deduced by comparison of optical rotation values with literature data and proved to be (S). This result was double-checked by chemical reduction of the aldehyde (S)-3b obtained via bioreduction using NaBH$_4$ to yield 2-methyl-3-phenyl-1-propanol (3c), which was proven to be (S)-configured on the basis of its optical rotation. Overall, the stereochemical outcome of the reduction of 3a nicely matched our previous results, as may be expected since substrates 1a-3a represent a structurally homologous series: while YqjM and OPR1 furnished (R)-3b with modest stereoselectivities (e.e.$_{max}$ 53% using OPR1), OPR3, NCR and OYE1-3 gave predominantly (S)-3b in up to 96% e.e. In view of these results, the stereochemical assignment of 3b—reported to be (R) (For the stereoselective bioreduction of α-methylcinnamaldehyde see: A. Müller, B. Hauer, B.

Rosche, *Biotechnol. Bioeng.* 2007, 98, 22-29)—have to be corrected to be (S). Consequently, the docking considerations to explain a stereochemical 'switch' of OYE1-3 and NCR between 2-methylpent-2-enal and 3a are invalid.

2.4 Conclusions

A convenient chemo-enzymatic synthesis for the fragrance aldehydes Lilial™ (1b) and Helional™ (2b) was developed via asymmetric bioreduction of α-methyldihydrocinnamaldehyde derivatives 1a and 2a catalysed by cloned and over-expressed ene-reductases. Whereas (R)-1b and (R)-2b were formed in modest e.e.s using YqjM and OPR1, NCR and OYEs 1-3 yielded (S)-antipodes in up to 96% e.e., when the reactions were run in an aqueous-organic biphasic system containing t-butyl methyl ether (20%, v:v). The stereochemical outcome of the reduction of α-methylcinnamaldehyde 3a using NCR and OYE1-3—previously reported to be (R) (For the stereoselective bioreduction of α-methylcinnamaldehyde see: A. Müller, B. Hauer, B. Rosche, *Biotechnol. Bioeng.* 2007, 98, 22-29)—was unambiguously corrected to be (S).

The documents as cited herein are all incorporated by reference.

TABLE 6

List of SEQ ID Nos

| Designation | Organism | Type | SEQ ID NO: |
|---|---|---|---|
| OYE1 | | AS | 1 |
| OYE2 | | AS | 2 |
| OYE2 | | AS | 3 |
| OPR1 | | AS | 4 |
| OPR3 | | AS | 5 |
| YqjM | | AS | 6 |
| NCR | | AS | 7 |

AS Amino acid sequence
NS Nucleic acid sequence

The invention claimed is:

1. An enzymatically catalyzed method for the production of an aldehyde compound of the general formula (I)

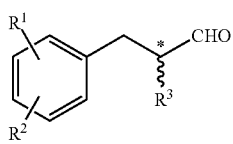

(I)

wherein
R$^1$ and R$^2$ represent together a group of the formula —O—R$^4$—O—, wherein R$^4$ represents an optionally substituted alkylen or alkenylen group; and
R$^3$ represents alkyl or alkoxy;
which method comprises:
a) enzymatically reducing a compound of formula II

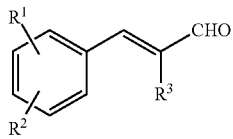

(II)

wherein
R$^1$, R$^2$ and R$^3$ are as defined above,
in an aqueous reaction medium comprising in a proportion of 5 to 40 vol.-% as a co-solvent at least one non-symmetric ether compound of the formula III

R$^5$—O—R$^6$  (III)

wherein
one of the residues R$^5$ and R$^6$ is a branched C$_3$-C$_8$ alkyl group, and the other is a C$_1$-C$_6$ alkyl group and also containing at least one reductase enzyme and at least one cofactor;
wherein said reductase is
an Old Yellow Enzyme 1 (OYE1) comprising the amino acid sequence of SEQ ID NO: 1, or a sequence having at least 95% sequence identity with said SEQ ID NO: 1 and being capable of hydrogenating a compound of formula II at position C2/C3; and
b) optionally isolating said compound of formula I in the form of a substantially pure stereoisomer or as a mixture of stereoisomers.

2. The method of claim 1, wherein said co-solvent is a t-butyl alkyl ether.

3. The method of claim 1, wherein reaction is performed in the presence of NADH or NADPH as cofactor.

4. The method of claim 1, wherein reduction reaction is coupled to a cofactor-recycling reaction.

5. The method of claim 4, wherein oxidized cofactor NAD is recycled by coupling to the glucose dehydrogenase catalyzed oxidation of glucose (forming gluconolactone and regenerating NADH).

6. The method of claim 1, wherein the enzymes involved are present in the reaction medium either in dissolved, dispersed or immobilized form.

7. The method of claim 1, wherein the reaction medium is buffered to a pH in the range of 6.5 to 8.5.

8. The method of claim 1, wherein the reaction temperature is in the range of 10 to 50° C.

9. The method of claim 8, wherein the reaction temperature is in the range of 20 to 40° C.

10. The method of claim 4, wherein the cofactor-recycling reaction is an enzymatic cofactor-recycling reaction.

* * * * *